United States Patent [19]

Kikumoto et al.

[11] 4,310,534

[45] Jan. 12, 1982

[54] PHARMACEUTICALLY ACTIVE 2-(4-AMINOBUTOXY)STILBENES

[75] Inventors: Ryoji Kikumoto, Machida; Akihiro Tobe, Kawasaki; Harukazu Fukami, Yokohama; Mitsuo Egawa, Yokohama; Kunihiro Ninomiya, Machida, all of Japan

[73] Assignee: Mitsubishi Chemical Industries Limited, Tokyo, Japan

[21] Appl. No.: 173,476

[22] Filed: Jul. 30, 1980

[30] Foreign Application Priority Data

Aug. 16, 1979 [JP] Japan .................................. 54/104218

[51] Int. Cl.$^3$ ............................................ A61Y 31/445
[52] U.S. Cl. ...................................... 424/267; 542/459
[58] Field of Search ......................... 542/459; 424/267

Primary Examiner—Stanley J. Freidman
Attorney, Agent, or Firm—Oblon, Fisher, Spivak, McClelland & Maier

[57] ABSTRACT 2-(4-aminobutoxy)stilbenes are prepared and found useful as pharmaceutical agents, particularly as anticonvulsants and skeletal muscle relaxants.

2 Claims, No Drawings

PHARMACEUTICALLY ACTIVE 2-(4-AMINOBUTOXY)STILBENES

BACKGROUND OF THE INVENTION

1. Field of the Invention

This invention relates to 2-(4-aminobutoxy)stilbenes and their acid addition salts which are pharmacologically active as anticonvulsants and skeletal muscle relaxants.

2. Description of the Prior Art

British Pat. No. 1,307,436 discloses 2-(2-aminoethoxy)stilbenes and 2-(3-aminopropoxy)stilbenes, which possess analgesic activity, while they do not possess anticonvulsant activity which is a characteristic feature of the compounds of this invention. On the other hand, the compound of this invention possess little, if any, analgesic activity.

SUMMARY OF THE INVENTION

Accordingly, it is an object of this invention to provide novel 2-(4-aminobutoxy)stilbenes having superior anti-convulsant activity.

This and other objects of this invention as will hereinafter become clear have been attained by providing compounds of the formula (I):

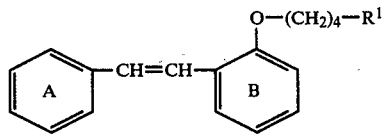

wherein $R^1$ is

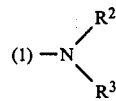

wherein $R^2$ and $R^3$ are each hydrogen and $C_1$-$C_3$ alkyl,

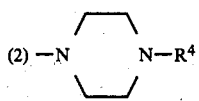

wherein $R^4$ is $C_1$-$C_3$ alkyl which may be substituted with hydroxy, or (3) hydroxypiperidino, and

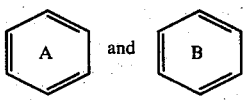

are benzene rings, at least one of which contains one or more substituents selected from hydrogen, $C_1$-$C_3$ alkyl, $C_1$-$C_3$ alkoxy,

wherein $R^5$ and $R^6$ are each $C_1$-$C_3$ alkyl, nitro and

wherein $R^7$ is $C_1$-$C_3$ alkyl, and the acid addition salts thereof.

This invention also relates to a method of treating convulsions and seizures or relieving skeletal muscle spasm in warm-blooded animals which comprises administering to said animals an effective amount for treatment of convulsions and seizures or relief of skeletal muscle spasm of a compound of the formula (I) or the acid addition salt thereof.

DESCRIPTION OF THE PREFERRED EMBODIMENTS

As summarized above, this invention relates to a group of compounds useful as pharmaceutical agents, which compounds are represented by the formula (I):

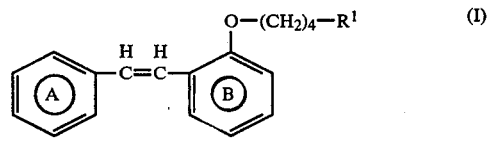

In Formula (I), $R^1$ is

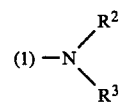

wherein $R^2$ and $R^3$ are each hydrogen or $C_1$-$C_3$ alkyl,

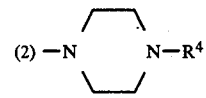

wherein $R^4$ is $C_1$-$C_3$ alkyl which may be substituted with hydroxy or (3) hydroxypiperidino.

Specific examples of the group

include amino, dimethylamino, methylamino, dipropylamino and the like, while specific examples of the group

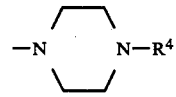

include 4-methyl-1-piperazinyl, 4-(2-hydroxyethyl)-1-piperazinyl, 4-ethyl-1-piperazinyl, 4-propyl-1-piperazinyl, 4-(3-hydroxypropyl)-1-piperazinyl and the like.

Also in Formula (I), at least one of the benzene rings

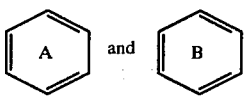

contains one or more substituents selected from halogen, $C_1$–$C_3$ alkyl, $C_1$–$C_3$ alkoxy,

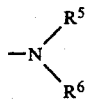

wherein $R^5$ and $R^6$ are each $C_1$–$C_3$ alkyl, nitro, and

wherein $R^7$ is $C_1$–$C_3$ alkyl.

The $C_1$–$C_3$ alkyl groups include methyl, ethyl, propyl and isopropyl. The $C_1$–$C_3$ alkoxy groups include methoxy, ethoxy, propoxy and isopropoxy. Exemplary of the group

are dimethylamino, diethylamino, dipropylamino and the like. The group

is exemplified by methoxycarbonyl, ethoxycarbonyl, propoxycarbonyl and the like.

Specific examples of the compound of Formula (I) include:
2-(4-dimethylaminobutoxy)-2′-chlorostilbene,
2-(4-dimethylaminobutoxy)-3′-chlorostilbene,
2-(4-dimethylaminobutoxy)-4′-fluorostilbene,
2-(4-diethylaminobutoxy)-4′-fluorostilbene,
2-{4-(3-hydroxypiperidino)butoxy}-4′-fluorostilbene,
2-{4-(4-methyl-1-piperazinyl)butoxy}-4′-fluorostilbene,
2-(4-dimethylaminobutoxy)-2′-methoxystilbene,
2-(4-dimethylaminobutoxy)-3-methoxystilbene,
2-{4-(4-methyl-1-piperazinyl)butoxy}-3-methoxystilbene,
2-{(4-(4-propyl-1-piperazinyl)butoxy}-3′-methoxystilbene,
2-(4-dipropylaminobutoxy)-2′-dimethylaminostilbene,
2-(4-dimethylaminobutoxy)-2′-dimethylaminostilbene,
2-(4-dimethylaminobutoxy)-2′,4′-dichlorostilbene,
2-{4-[4-(2-hydroxyethyl)-1-piperazinyl]butoxy}-3′-chlorostilbene,
2-(4-dimethylaminobutoxy)-4′-nitrostilbene,
2-(4-dimethylaminobutoxy)-2′-methoxycarbonylstilbene,
2-(4-dimethylaminobutoxy)-2′-methylstilbene,
2-{4-(4-methyl-1-piperazinyl)butoxy}-2′-methylstilbene,
2-(4-dimethylaminobutoxy)-2′-fluorostilbene,
2-{4-(4-hydroxypiperidino)butoxy}-4′-fluorostilbene,
2-{4-[4-(2-hydroxyethyl)-1-piperazinyl]butoxy}-2′-chlorostilbene,
2-{4-(4-methyl-1-piperazinyl)butoxy}-3′-chlorostilbene,
2-(4-dimethylaminobutoxy)-4′-chlorostilbene,
2-{4-(4-methyl-1-piperazinyl)butoxy}-3′,4′-dichlorostilbene,
2-(4-dimethylaminobutoxy)-5-chlorostilbene,
2-{4-[4-(2-hydroxyethyl)-1-piperazinyl]butoxy}-4′-fluorostilbene,
2-{4-(4-methyl-1-piperazinyl)butoxy}-2′-fluorostilbene, and
2-(4-dimethylaminobutoxy)-4′-dimethylaminostilbene.

The present invention also encompasses pharmaceutically acceptable acid addition salts of the compounds of Formula (I). Illustrative of such acid addition salts are hydrochloride, hydrobromide, sulfate, phosphate, nitrate, acetate, oxalate, succinate, adipate, propionate, tartarate, maleate, citrate, benzoate, toluenesulfonate, methanesulfonate and the like.

The compounds of the above Formula (I) may be prepared by reacting a 2-(4-halogenobutoxy)-stilbene having the formula (II):

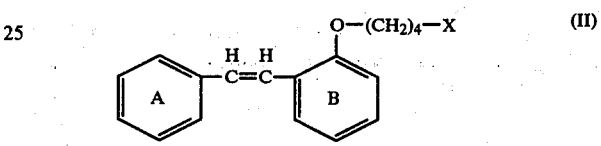

wherein X is halogen and the rings

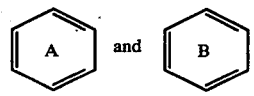

are as defined in Formula (I), with an amine having the formula (III):

wherein $R^1$ is as defined in Formula (I).

The 2-(4-halogenobutoxy)stilbene (II) as one of the starting materials is derived from the corresponding hydroxystilbene by reacting it with a 1,4-dihalogenobutane in the presence of a base.

In the above reaction, one mole of amine (III) is consumed for each mole of 2-(4-halogenobutoxy)stilbene (II). The amine can be used in excess in order to increase the rate of reaction. Usually the amine is used in an amount of 1 to 100 moles per mole of 2-(4-halogenobutoxy)stilbene. The reaction proceeds sufficiently even in the absence of solvent, but an inert solvent may be used in order to effect the reaction in a homogeneous system. Useful solvents include water, dioxane, tetrahydrofuran, dimethyl sulfoxide, lower alcohols, dimethylformamide and mixtures of two or more of these solvents.

The reaction temperature is not critical, but usually ranges from ambient temperature to 150° C.

The reaction time depends on the reaction temperature and the reactivity of the starting materials, and usually does not exceed 40 hours.

A base may be added in order to bind the hydrogen halide formed by the reaction and thereby accelerate the reaction. The bases which can be used include inorganic bases such as potassium hydroxide, sodium hydroxide, potassium carbonate and sodium carbonate, and tertiary amines such as pyridine and triethylamine. Usually the base is used in an amount of 1 to 5 moles per mole of 2-(4-halogenobutoxy)stilbene.

In the case where no base is added, the 2-(4-aminobutoxy) stilbene product will further react with the hydrogen halide formed by the reaction whereby it is converted into its acid addition salt (hydrohalide). In order to obtain any desired acid addition salt from the reaction mixture, the excess amine and solvent are distilled off and an aqueous solution of a strong base such as sodium hydroxide or potassium hydroxide is added to convert the acid addition salt of 2-(4-aminobutoxy)stilbene into the free base, which is then extracted with a suitable solvent such as ether, chloroform or benzene. The extract is neutralized with the appropriate acid to give the desired acid addition salt of 2-(4-aminobutoxy)-stilbene.

The 2-(4-aminobutoxy)stilbene and its acid addition salt thus obtained may be purified by recrystallization from a suitable solvent such as alcohol-ether.

The compounds of this invention exhibit superior anti-convulsive effects. In this respect, preferred compounds are those of Formula (I) wherein $R^1$ is

wherein $R^2$ and $R^3$ are each a $C_1$–$C_3$ alkyl,

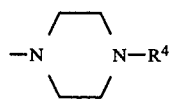

wherein $R^4$ is as defined above, or hydroxypiperidino; and at least one of the benzene rings

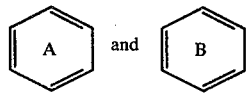

contains one or more substituents selected from halogen and $C_1$–$C_3$ alkoxy. Specific examples of the preferred compounds include:
2-(4-dimethylaminobutoxy)-2'-chlorostilbene,
2-(4-dimethylaminobutoxy)-3'-chlorostilbene,
2-(4-dimethylaminobutoxy)-4'-fluorostilbene,
2-(4-diethylaminobutoxy)-4'-fluorostilbene,
2-4-(3-hydroxypiperidino)butoxy-4'-fluorostilbene,
2-(4-(4-methyl-1-piperazinyl)butoxy-4'-fluorostilbene,
2-(4-dimethylaminobutoxy)-2'-methoxystilbene,
2-(4-dimethylaminobutoxy)-3-methoxystilbene,
2-4-(4-methyl-1-piperazinyl)butoxy-3-methoxystilbene, and
2-4-(4-propyl-1-piperazinyl)butoxy-3-methoxystilbene.

Pharmacological effects of particularly preferred compounds were tested. Anticonvulsive activities of these compounds were evaluated in the following manner and the results are reported in Table 1 below along with the data of anti-convulsive activities of known antiepileptics, methotoin which is effective for grand mal and trimethadione which is effective for petit mal.

As the test animals ddy male mice (20–22 g in body weight) and Wistar male rats (150–170 g) were used. Anticonvulsive activity was assessed by inhibitory effects on pentylentetrazol (PTZ)-induced convulsion and maximum electric shock (MES) convulsion, using eight mice for each group. The anti-PTZ-convulsive activity was evaluated from inhibition against tonic extensor (TE) induced by intraperitoneal administration of 100 mg/kg PTZ [K. Nakamura, K. Ohashi, K. Nakatsuji, T. Hirooka, K. Fujimoto and S. Ose; Arch. Int. Pharmacodyn., 156, 261 (1965)]. The anti-MES-convulsive activity was evaluated from inhibition against tonic extensor developed by applying an electric shock to the mouse through electrodes attached to the ear lobes [J. J. Piala, J. P. High, G. L. Hassert, Jr., J. C. Burke and B. N. Craver, J. Pharmacol. exp. Therap., 127, 55 (1959)]. The results are expressed as 50% effective dose ($ED_{50}$, mg/kg po) or percent inhibition at a given dose. The values for $LD_{50}$ were determined by the Litchfield-Wilcoxon method [J. T. Litchfield and F. Wilcoxon, J. Pharmacol. exp. Therap., 96, 99 (1949)].

TABLE 1

| Compound | Anti-MES $ED_{50}$ (mg/kg) po | Anti-PTZ $ED_{50}$ (mg/kg) po | $LD_{50}$ (mg/kg) po |
|---|---|---|---|
| 2-(4-Dimethylaminobutoxy)-4'-fluorostilbene | >100 (14.3%) | 15.4 | >1200 |
| 2-4-(4-Methyl-1-piperazinyl)-butoxy-4'-flourostilbene | 39.0 | 17.7 | >1200 |
| 2-(4-Dimethylaminobutoxy)-3'-chlorostilbene | >50 (14.3%) | 23.9 | — |
| 2-(4-Dimethylaminobutoxy)-3-methoxystilbene | 40 | 21.6 | <1000 |
| 2-4-(4-Methyl-1-piperazinyl)-butoxy-3-methoxystilbene | 60 | 50.0 | 1000 |
| Methotoin | 91.3 | 51.9 | 475 |
| Trimethadione | 1180 | 230 | 2200 |

The values in parentheses denote % inhibition. In the above table, the second, fourth and fifth compounds have anticonvulsive activities superior to those of the control drugs. In particular, the second compound has an outstanding efficacy and a wide safety region.

The compounds of this invention which are effective as anticonvulsive therapeutic agents may be administered by any route. Both parenteral administration such as subcutaneous, intravenous, intramuscular or intraperitoneal injection and oral administration are possible.

The dose should be decided depending on various factors such as the age, condition and body weight of the patient, the type of concomitant treatment, if any, the frequency of administration, and the degree of the desired results of the treatment. In general a daily dose of 0.5 to 50 mg/kg-body weight; usually 1–30 mg/kg-body weight of active ingredient is applied one or more times a day. For oral administration the compounds of this invention may be used in the form of tablets, capsules, powders, liquids, elixirs, while for parenteral administration they may be used in the form of sterile liquids such as solutions or suspensions. When the active ingredients are used in the above-mentioned forms, a solid or liquid non-toxic pharmaceutical carrier may be incorporated in the formulations.

Conventional gelatine-type capsules are illustrative of the solid carrier. Alternatively, the active ingredient may be formulated into tablets or powder packages with or without an adjuvant. These capsules, tablets and powders are expected to contain generally 5 to 95%, preferably 25 to 90% by weight active ingredient. Thus dosage units of these forms will contain 5 to 500 mg, preferably 25 to 250 mg of active ingredient.

Liquid carriers which can be used include water, oils of animal or vegetable, origin such as petroleum, peanut oil, soybean oil, mineral oil and sesame oil and synthetic oils. However, in general, preferred liquid carriers are isotonic saline solution, aqueous solutions of dextrose or similar saccharide and glycols such as ethylene glycol, propylene glycol and polyethylene glycol. For example, an injection prepared with isotonic saline solution as carrier should contain 0.5 to 20%, preferably 1 to 10% by weight active ingredient.

In the case of liquids for oral administration, they are preferably in the form of suspensions or syrups containing 0.5 to 10% by weight active ingredient. In such cases, a water-like vehicle containing a flavoring agent, syrup and/or pharmaceutical micelles is used as carrier. As above mentioned in detail, the compounds of this invention possess superior anticonvulsive effects and therefore can be used effectively in the treatment of epilepsy.

Having generally described the invention, a more complete understanding can be obtained by reference to certain specific examples, which are included for purposes of illustration only and are not intended to be limiting unless otherwise specified.

EXAMPLES

In a mixture of 50 ml of tetrahydrofuran and 50 ml of aqueous 50% dimethylamine solution 5 g of 2-(4-bromobutoxy)-2'-chlorostilbene was dissolved and the resulting solution was stirred for 20 hours at ambient temperature. After the reaction was complete, the solvent was distilled off at reduced pressure. An aqueous 2 N NaOH solution was added to the residue and the mixture was extracted with ether. The extract was washed with saturated sodium chloride solution and dried over anhydrous sodium sulfate. To the extract an ethanolic 20% hydrogen chloride was added to give 2-(4-dimethylaminobutoxy)-2'-chlorostilbene hydrochloride as a precipitate, which was then collected by filtration and recrystallized from ethanol-ether. Yield 4.7 g (94%). The data of melting point and elemental analysis are reported in the line of No. 1 in Table 2. Various compounds were also prepared in a similar manner. The data for these compounds are shown in Table 2.

TABLE 2

| No. | R¹ | A* | B* | Addition Salt | m.p. (°C.) | Elemental analysis Upper: Calc. Lower: Found C | H | N | IR Spectrum (cm⁻¹) |
|---|---|---|---|---|---|---|---|---|---|
| 1 | N(CH₃)₂ | 2'-Cl | H | HCl | 165–166 | 65.58 / 65.47 | 6.88 / 6.91 | 3.82 / 3.91 | |
| 2 | N⌒N-CH₂CH₂OH | 2'-Cl | H | 2HCl | 176–178 | 61.09 / 61.21 | 7.05 / 7.00 | 5.93 / 5.87 | |
| 3 | N(CH₃)₂ | 3'-Cl | H | HCl | 95 | 65.58 / 65.47 | 6.88 / 6.90 | 3.82 / 3.92 | |
| 4 | N⌒N-CH₃ | 3'-Cl | H | 2HCl | 215–217 | 60.33 / 60.34 | 6.92 / 6.85 | 6.12 / 6.21 | |
| 5 | N(CH₃)₂ | 4'-Cl | H | HCl | 145–148 | 65.58 / 65.70 | 6.88 / 7.00 | 3.82 / 3.79 | |
| 6 | N⌒N-CH₃ | 3',4'-diCl | H | 2HCl | 210–213 | 56.11 / 56.13 | 6.14 / 6.14 | 5.69 / 5.75 | |
| 7 | N(CH₃)₂ | 2',4'-diCl | H | HCl | 149 | 59.94 / 60.02 | 6.04 / 6.11 | 3.50 / 3.46 | |
| 8 | N(CH₃)₂ | H | 5-Cl | HCl | 113–115 | 65.58 / 65.55 | 6.88 / 6.92 | 3.82 / 3.90 | |
| 9 | N(CH₃)₂ | 4'-F | H | HCl | 113 | 68.66 / 68.73 | 7.20 / 7.18 | 4.00 / 3.99 | |
| 10 | N⌒N-CH₃ | 4'-F | H | 2HCl | 220–224 (d) | 62.58 / 62.46 | 7.08 / 6.98 | 6.35 / 6.21 | |
| 11 | N⌒-OH | 4'-F | H | HCl | 177–178 | 68.05 / 67.97 | 7.20 / 7.31 | 3.45 / 3.34 | |
| 12 | N⌒N-CH₂CH₂OH | 4'-F | H | 2HCl | 190–191 | 63.29 / 63.21 | 7.30 / 7.21 | 6.15 / 6.30 | |
| 13 | N(CH₃)₂ | 2'-F | H | HCl | 123–124 | 68.66 / 68.82 | 7.20 / 7.15 | 4.00 / 3.96 | |

TABLE 2-continued

| No. | R¹ | A* | B* | Addition Salt | m.p. (°C.) | Elemental analysis Upper: Calc. Lower: Found C | H | N | IR Spectrum (cm⁻¹) |
|---|---|---|---|---|---|---|---|---|---|
| 14 | [N-methylpiperazinyl] | 2'-F | H | 2HCl | 141–143 | 62.58 / 62.46 | 7.08 / 7.02 | 6.35 / 6.27 | |
| 15 | N(CH$_3$)$_2$ | 2'-OCH$_3$ | H | HCl | powder | 69.69 / 69.80 | 7.30 / 7.77 | 3.87 / 3.91 | 3300,2920 2650,760 |
| 16 | N(CH$_3$)$_2$ | H | 3-OCH$_3$ | HCl | 164–165 | 69.69 / 68.74 | 7.80 / 7.69 | 3.87 / 3.76 | |
| 17 | [N-methylpiperazinyl] | H | 3-OCH$_3$ | 2HCl | 172–175 | 63.57 / 63.50 | 7.56 / 7.39 | 6.18 / 6.30 | |
| 18 | N(CH$_3$)$_2$ | 2'-CH$_3$ | H | HCl | 148–149 | 72.92 / 73.01 | 8.16 / 8.02 | 4.05 / 4.00 | |
| 19 | [N-methylpiperazinyl] | 2'-CH$_3$ | H | 2HCl | 205–208 | 65.89 / 65.71 | 7.83 / 7.84 | 6.40 / 6.50 | |
| 20 | N(CH$_3$)$_2$ | 4'-N(CH$_3$)$_2$ | H | 2HCl | Hygroscopic | 70.47 / 70.53 | 8.33 / 8.46 | 7.47 / 7.51 | 3400,2950 2650,750 |
| 21 | N(CH$_3$)$_2$ | 4'-NO$_2$ | H | HCl | 195–197 | 63.74 / 63.59 | 6.69 / 6.72 | 7.43 / 7.50 | |
| 22 | N(CH$_3$)$_2$ | 2'-CO$_2$CH$_3$ | H | HCl | 135–137 | 67.77 / 67.81 | 7.24 / 7.30 | 3.59 / 3.42 | |
| 23 | [hydroxypiperidino] | 4'-F | H | HCl | 154–156 | 68.05 / 68.32 | 7.20 / 7.11 | 3.45 / 3.50 | |

*This column denotes the substituent and its position of the benzene ring.
"H" indicates that the ring contains no substituent.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A compound having the formula (I):

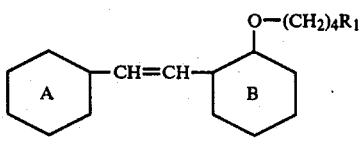

wherein $R_1$ is hydroxypiperidino and wherein at least one of the benzene rings of said compounds is substituted with at least one substituent selected from the group consisting of halogen, $C_1$-$C_3$ alkyl, $C_1$-$C_3$ alkoxy, —NR$^5$R$^6$ wherein R$^5$ and R$^6$ are each $C_1$-$C_3$ alkyl, nitro and $$R^7OC(=O)-$$

wherein $R^7$ is $C_1$-$C_3$ alkyl, and an acid addition salt thereof.

2. A therapeutic composition, comprising: a therapeutically effective amount of the compound of claim 1 and a pharmaceutically acceptable carrier.

* * * * *

UNITED STATES PATENT AND TRADEMARK OFFICE
CERTIFICATE OF CORRECTION

PATENT NO. : 4,310,534
DATED : January 12, 1982
INVENTOR(S) : Ryoji Kikumoto et al It is certified that error appears in the above—identified patent and that said Letters Patent is hereby corrected as shown below:

Cancel formula in Claim 1 and substitute the new formula shown:

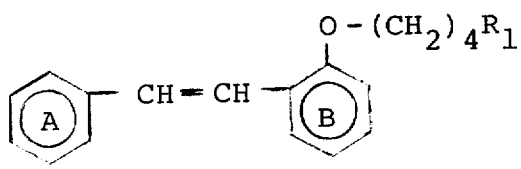

Signed and Sealed this

Fifteenth Day of June 1982

[SEAL]

Attest:

GERALD J. MOSSINGHOFF

Attesting Officer  Commissioner of Patents and Trademarks